US009695457B2

(12) United States Patent
Somaiya

(10) Patent No.: US 9,695,457 B2
(45) Date of Patent: Jul. 4, 2017

(54) RAPID DETECTION OF BACTERIA USING MASS SPECTROMETRIC ANALYSIS

(75) Inventor: Pranav Somaiya, Harrow (GB)

(73) Assignee: OM Research Limited, London (GB)

( * ) Notice: Subject to any disclaimer, the term of this patent is extended or adjusted under 35 U.S.C. 154(b) by 126 days.

(21) Appl. No.: 13/147,951

(22) PCT Filed: Feb. 5, 2010

(86) PCT No.: PCT/GB2010/000219
§ 371 (c)(1),
(2), (4) Date: Aug. 4, 2011

(87) PCT Pub. No.: WO2010/089569
PCT Pub. Date: Aug. 12, 2010

(65) Prior Publication Data
US 2011/0294158 A1    Dec. 1, 2011

(30) Foreign Application Priority Data

Feb. 6, 2009    (GB) .................................. 0902033.0

(51) Int. Cl.
| | | |
|---|---|---|
| C12Q 1/04 | (2006.01) | |
| C12M 1/34 | (2006.01) | |
| C12N 1/20 | (2006.01) | |
| C12Q 1/14 | (2006.01) | |

(52) U.S. Cl.
CPC ........ *C12Q 1/04* (2013.01); *C12Q 1/14* (2013.01)

(58) Field of Classification Search
None
See application file for complete search history.

(56) References Cited

U.S. PATENT DOCUMENTS

| | | | | |
|---|---|---|---|---|
| 6,565,808 B2 * | 5/2003 | Hudak et al. | ................. | 422/411 |
| 2004/0234952 A1 | 11/2004 | Kallow et al. | | |

FOREIGN PATENT DOCUMENTS

| | | |
|---|---|---|
| EP | 1942194 | 8/2007 |
| GB | 2438066 | 11/2007 |

OTHER PUBLICATIONS

Demirev et al. "Mass spectrometry for rapid characterization of microorganisms", Annu. Rev. Anal Chem. 1: 71-93, 2008.*
Bernardo et al. "Identification of *Staphylococcus aureus* exotoxins by combined sodium dodecyl sulfate gel electrophoresis and matrix-assisted laser desorption/ionization-time of flight mass spectrometry" Proteomics 2: 740-6, 2002.*
Mo Bio Laboratories, Inc. "LB Broth (Lennox) Powder Growth Media Instructions for Use", Product Manual, available online, 2005.*
Demirev et al. "Chemical and biological weapons: Current concepts for future defenses", Johns Hopkins APL Technical Digest 26(4): 321-333, 2005.*
University of South Carolina "Autoclave Safety Policy" available online at <http://www.sc.edu/ehs/Biosafety/Autoclave%20Safety%20Policy.pdf>, issue date Mar. 3, 2008.*
Camara et al. "Discrimination between wild-type and ampicillin-resistant *Escherichia coli* by matrix-assisted laser desorption/ionization time-of-flight mass spectrometry", Analytical and Bioanalytical Chemistry 389:1633-8, 2007.*
Smole, Sandra C. et al., "Sample preparation of Gram-positive bacteria for identification by matrix assisted laser desorption/ionization time-of-flight," Journal of Microbiological Methods, vol. 48, pp. 107-155,(2002).
Bright, John J., et al., "Rapid typing of bacteria using matrix-assisted laser desorption ionixation time-of-flight mass spectrometry and pattern recognition software," Journal of Microbiological Methods, vol. 48, pp. 127-138, (2002).
Cunningham, R., et al., "Effect on MRSA transmission of rapid PCR testing of patients admitted to critical care," Journal of Hospital Infection, vol. 65, pp. 24-28, (2007).
Nour De San, et al., "Controlled Evaluation of the IDI-MRSA Assay for Detection of Colonization by Methicillin-Resistant *Staphylococcus aureus* in Diverse Mucocutaneous Specimens," Journal of Clinical Microbiology, Apr. 2007, pp. 1098-1101.
Jackson, et al., "Optimisation of intact cell MALDI method for fingerprinting of methicillin-resistant *Staphylococcus aureus*," Journal of Microbiological Methods, (2005), 62(3), pp. 273-284.
Jeyaratnam, et a., "Impact of rapid screening tests on acquisition of meticillin resistant *Staphylococcus aureaus*: cluster randomised crossover trial," BMJ, 336(7650), pp. 927-930.
Hardy, et al., "A study of the efficacy and cost-effectiveness of MRSA screening and monitoring on surgical wards using a new, rapid molecular test (EMMS)," BMC Health Sery Res, pp. 7:160.
Chediac-Tannoury et al., "Rapid MRSA detection by a latex kit," Clinical Laboratory Science, vol. 16., No. 4, pp. 198-202 (2003).
Edwards-Jones, et al., "Rapid discrimination between methicillin-sensitive and methicillin-resistant *Staphylococcus aureus* by intact cell specgtrometry," J Med. Microbiolgy, vol. 49, pp. 295-300.
Jackson, et al., "Determination and structural examination of potential biomarkers for Methicillin-resistant *Staphylococcus aureus*," Applications of Genomics and Proteomics for Analysis of Bacterial Biological Warfare Agents, IOS Press Delvecchio et al., pp. 149-154, (2003).
Du, et al., Identification of *Staphylococcus aureus* and determination of its methicillin resistance by matrix-assisted time-of-flight mass spectrometry, Analytical Chemistry, American Chem Society, vol. 74, No. 21, pp. 5487-5491.

* cited by examiner

*Primary Examiner* — Emily Cordas
(74) *Attorney, Agent, or Firm* — Gavrilovich, Dodd & Lindsey LLP

(57) ABSTRACT

Methods for the detection or diagnosis of a bacterial infection or colonization utilizing mass spectrometric analysis are provided. The methods involve short-term enrichment of samples followed by mass spectrometric analysis of biomarker profiles. Also provided are methods for preparing short-term enrichment cultures.

17 Claims, 7 Drawing Sheets

RAPID DETECTION OF BACTERIA USING MASS SPECTROMETRIC ANALYSIS

CROSS REFERENCE TO RELATED APPLICATIONS

This application is the U.S. national phase entry of PCT/GB2010/000219 with an international filing date of Feb. 5, 2010, which claims the benefit of British Patent Application No. 0902033.0, filed on Feb. 6, 2009, the entire disclosures of which are incorporated herein by reference.

FIELD OF THE INVENTION

This invention relates to a method for the detection or diagnosis of a bacterial infection or colonisation. More specifically, it relates to detection of the presence or absence of particular bacteria using mass spectrometric analysis, in particular MALDI-TOF mass spectrometric analysis.

BACKGROUND

For effective management of bacterial infection, early diagnosis of the presence of an infection/colonisation and swift treatment is essential. A particular problem in clinical environments such as hospitals is detecting, isolating, and treating patients and health workers carrying 'superbugs' such as MRSA (methicillin-resistant *Staphylococcus aureus*) before they come into contact with vulnerable patients. The prevalence of infections caused by MRSA has been increasing for several years in many countries around the world.

Reports from the UK National Audit Office state that at any one time, 9 percent of NHS hospital patients are suffering from an infection such as MRSA, acquired whilst in surgery or as an inpatient on the hospital wards. These 'nosocomial' infections affect 100,000 people annually, costing the National Health Service £1 billion (€ 1.5 bn), and causing up to 5,000 deaths. The US Centre for Disease Control and Prevention estimates that between 60,000 and 80,000 Americans die each year from nosocomial infections, and the cause in the majority of cases is *S. aureus*.

Some strains of MRSA are particularly successful at spreading between patients and may also spread between hospitals, for example when colonised patients or staff move from one hospital to another. These strains are known as epidemic MRSA (EMRSA). During the 1990s there was a marked increase in infections caused by MRSA in hospitals in the UK due to the emergence and spread of two particular stains of EMRSA known as EMRSA-15 and EMRSA-16. In 2002, a new epidemic strain, EMRSA-17, was described in the UK. This strain is more resistant than any previous UK EMRSA strains.

Older methods of screening are too slow to effectively prevent the spread of hospital-acquired infections and can be very expensive and labour-intensive. Some existing methods are also inaccurate and may suffer from problems with specificity and sensitivity. Laboratory screening for MRSA is therefore a complex balance between speed of result, sensitivity, specificity and cost.

Standard methods for diagnosis of MRSA involve overnight culturing of the bacteria followed by visual identification and verification of MRSA colonies. Agar plate-based methods are the most common, using either selective or non-selective media. Broths or slopes (which may also be selective or non-selective) can also be used. These methods have been practised for many years, and are generally quite specific and sensitive. However, they can provide answers only after 3-5 days, which is of little use in a hospital setting, from the perspective of infection control.

As a result, newer methods, in particular PCR based methods, have been developed with the aim of providing results more rapidly. PCR results can generally be obtained in one working day, compared to three working days for culture methods, although this is still too long if the spread of the bacteria is to be effectively controlled.

The 'first generation' of PCR-based methods (e.g. References 1-4) rely on the presence of a combination of the methicillin resistance gene, mecA, with one or more other genes specific to *S. aureus* (e.g. femA or nuc). These methods have major drawbacks in the form of false positive rates, costs, and lack of automation, and are mostly only suitable for use with pure cultures, not screening of clinical swabs.

The more recently developed generation of PCR-based methods (e.g. References 5-8) have had some success. For example, the IDI-MRSA PCR test, in which a single genetic sequence is detected specific to MRSA, is now approved for use in nasal swabs for colonisation. These methods still suffer from problems, however. Using nasal swabs only, they will only catch 50% of the patients who are colonised, and none of those with bacteraemia.

Other methods which have been developed include the latex agglutination method (Reference 9). The most commonly used commercial test relies on the presence of Protein A and PBP2A which, combined together, point toward MRSA. However, this test has sensitivity and specificity problems.

There is a need for a new method for the rapid diagnosis of bacterial infections, such as MRSA, which overcomes the sensitivity and specificity problems of currently available methods, and can be performed quickly, easily and at low cost.

SUMMARY OF THE INVENTION

The present invention provides detection methods for bacterial infections or colonisations, which utilise short-term enrichment followed by mass spectrometric analysis of the bacterial biomarker profile.

Accordingly, in one aspect, the invention provides a method for detection of the presence or absence of particular bacteria in a sample, the method comprising:
i) enriching the sample by culturing the bacteria present in the sample, for a period of less than six hours;
ii) analysing the enriched sample by mass spectrometry, to obtain biomarker profile data for the sample;
iii) comparing the sample biomarker profile data with reference data, to determine the presence or absence of said particular bacteria in the sample;
wherein the reference data is obtained from a reference sample of said particular bacteria,
wherein the reference sample has been cultured for less than six hours.

In a related aspect, the invention provides a method for detection of the presence or absence of particular bacteria in a sample, the method comprising:
(i) enriching the sample by culturing until a detectable quantity of pre-modification biomarkers is produced in the sample;
(ii) analysing the enriched sample by mass spectrometry, to obtain biomarker profile data for the sample;

(iii) comparing the sample biomarker profile data with reference data, to determine the presence or absence of said particular bacteria in the sample;
wherein the reference data relates to pre-modification biomarkers produced by a reference sample of said particular bacteria.

In another related aspect, the invention provides a method for detection of the presence or absence of particular bacteria in a sample, the method comprising:
(i) enriching the sample by culturing the bacteria present in the sample;
(ii) analysing the enriched sample by mass spectrometry, to obtain biomarker profile data for the sample,
wherein the biomarker profile data comprises peaks corresponding to pre-modification biomarkers produced by the bacteria in the sample;
(iii) comparing the sample biomarker profile data with reference data, to determine the presence or absence of said particular bacteria in the sample;
wherein the reference data relates to pre-modification biomarkers produced by a reference sample of said particular bacteria.

A further related aspect of the invention provides a method for detection of the presence or absence of particular bacteria in a sample, the method comprising:
(i) enriching the sample by culturing the bacteria present in the sample;
(ii) analysing the enriched sample by mass spectrometry, to obtain biomarker profile data for the sample, wherein the biomarker profile data comprises peaks in the region below 1500 Da;
(iii) comparing the sample biomarker profile data with reference data, to determine the presence or absence of said particular bacteria in the sample;
wherein the reference data relates to peaks in the region below 1500 Da produced by a reference sample of said particular bacteria.

The methods of the invention are for detecting the presence or absence of particular bacteria in a sample i.e. for detecting a particular bacterial infection or colonisation of interest. The bacterial infection/colonisation to be detected is typically pre-determined and may comprise a particular bacterial strain, sub-species, species or genus. The reference data to which the sample mass spectrometric profile is compared in the methods of the invention is chosen according to the particular strain, species or genus of bacteria to be detected, as further described below. Any type of bacteria for which a short-term enrichment biomarker profile can be established, as described herein, may be detectable using the present methods.

Examples of bacteria which may be detected include Staphylococci (such as *S. aureus, S. afermentans, S. auricularis, S. capitis, S. caprae, S. cohnii, S. epidermidis, S. fells, S. haemolyticus, S. hominis, S. intermedius, S. lugdunensis, S. pettenkoferi, S. saprophyticus, S. schleiferi, S. simulans, S. vitulus, S. warner, S. xylosus*; preferably *Staphylococcus aureus*), *Clostridium* species (such as *C. difficile, C. botulinum, C. perfringens, C. tetani*; especially *C. difficile*), *Escherichia coli, Campylobacter* (such as *C. jejuni, C. coil and C. fetus*), *Salmonella, Pseudomonas, Shigella, Neisseria, Klebsiella, Vibrio, Legionella, H influenzae, H pylori, Bacillus, Listeria* as well as tuberculosis and leprosy.

In some preferred embodiments, the methods of the invention are used to detect the presence of Gram-positive bacteria. More preferably, the bacterium is *Staphylococcus*, such as *Staphylococcus aureus*. In particularly preferred embodiments, the bacterium is methicillin-resistant *Staphylococcus aureus* (MRSA). MRSA refers to certain strains of *Staphylococcus aureus* which are resistant to methicillin and similar antibiotics. In particular, it is useful to detect certain strains known as epidemic MRSA (EMRSA) for example EMRSA-15, EMRSA-16 and EMRSA-17.

The sample analysed in the methods of the invention may be any sample suspected of containing a particular bacterial infection or colonisation. Samples may be taken from humans or non-human animals, particularly mammals, or from a source which is not directly a living animal for example from food or from a building or an industrial plant, such from a hospital structure (e g hospital floors or furnishings), a water-containing system in a building (e g water supply, heating, cooling or air-conditioning system) or a food-processing plant. In preferred embodiments, the sample to be tested is a clinical sample taken from a human patient. It may be in the form of a blood sample, a tissue sample, a urine sample, a fecal sample, a gastric sample, a saliva sample, a cerebrospinal fluid sample or a swab, for example a nasal swab.

In some preferred embodiments, the sample is taken from a wound site, an ulcer, or a human screening site (e.g. nose, throat, groin, perineum, axilla).

Advantageously, the method may detect very small concentrations of bacteria. This may enable detection of colonisation as well as infection. Colonisation is defined as the presence of proliferating bacteria without a host response and usually involves lower concentrations of bacteria thus making it harder to detect (see e.g. References 16 and 17).

Advantageously, diagnosis may be possible starting from a sample containing a wound concentration of bacteria.

The method may allow detection of concentrations as low as 1 cfu/ml (colony forming units/ml). 1 cfu/ml is equal to 1 bacterium that can form a colony by binary fission. This means that there is 1 viable colony forming organism in that ml of sample. Microbiology based detection uses cfu/ml as the standard measurement of microbial concentration.

In some embodiments, the sample, before enrichment, may contain bacteria concentration of about $10^9$ cfu/ml or below; about $10^8$ cfu/ml or below; about $10^7$ cfu/or below; about $10^6$ cfu/ml or below; about $10^5$ cfu/ml or below; about $10^4$ cfu/ml or below; about $10^3$ cfu/ml or below; about $10^2$ cfu/ml or below; about 10 cfu/ml or below; or about 1 cfu/ml or below.

In some embodiments the sample, before enrichment, contains bacteria at a concentration of about 1 cfu/ml to about $10^9$ cfu/ml; about 10 cfu/ml to about $10^9$ cfu/ml; about $10^2$ cfu/ml to about $10^9$ cfu/ml; about $10^3$ cfu/ml to about $10^9$ cfu/ml; about $10^4$ cfu/ml to about $10^9$ cfu/ml; or about $10^5$ cfu/ml to about $10^9$ cfu/ml.

The sample is prepared for analysis by a short-term enrichment process. The number of bacteria and hence the amount of bacterially produced proteins in the sample are increased in this process.

Enrichment of the test sample is carried out by culturing the sample. Culturing is preferably carried out for a pre-determined time period, which is preferably for less than 6 hours, for 4 hours or less, for 2 hours or less, for 1 hour or less, or for 30 minutes or less. For practical reasons, a preferred minimum time period may be 5 minutes, 15 minutes, 30 minutes, 1 hour, or 90 minutes.

In some embodiments of the invention, the biomarker profile data for the sample comprises mass spectrometric peaks with m/z values in the region below 1500. This typically corresponds to molecules having molecular mass in the region below 1500 Da. The biomarker profile data for the sample may therefore be said to comprise mass spectrometric peaks in the region below 1500 Da. These peaks may be present in addition to peaks which are also present in a 24 h-culture biomarker profile for the bacteria.

The profile data obtained from analysis of the short-term enriched culture preferably includes data relating to pre-modification biomarkers produced by said particular bacteria. The mass spectrometric profile therefore comprises peaks corresponding to said pre-modification biomarkers produced by the bacteria in the sample.

In some embodiments, the pre-modification biomarkers may comprise pre-modification proteins and/or peptidoglycans produced by said particular bacteria. The pre-modification biomarkers may comprise pre-PTM (post-translational modification) proteins. In certain embodiments, the pre-modification proteins may comprise unglycated cell wall peptides. In some preferred cases, these pre-modification proteins comprise proteins or peptidoglycans with a molecular mass below 1500 Da.

A wide variety of culture media and culture conditions are known to those skilled in the art, including plates (e.g. Agar plates), slopes, slants or broths. The exact nature of the culture media which may be used in the short-term enrichment culture step of the methods of the invention may be varied, to optimise enrichment and to ensure reproducibility of the biomarker profile. In some embodiments of the invention, the culturing is carried out in a broth, such as a Brain Heart Infusion (BHI) broth, a Mueller-Hinton Broth, an Anaerobic broth or a Nutrient Broth. In preferred embodiments a Brain Heart Infusion Broth is used. Optionally, a broth may contain additives such as antibiotics.

The present inventor has developed a novel culturing and enrichment method for bacterial samples, which is particularly advantageous when used in conjunction with the MS analysis method of the present invention. Accordingly, a further aspect of the present invention provides a method of obtaining an enriched bacteria-containing sample, including the steps of:
inoculating a bacteria-containing sample into a broth;
culturing the sample-containing broth for a period of less than 6 hours;
separating the enriched sample from the sample-containing broth by centrifugation. Culturing the sample preferably comprises incubation in a water bath.

An enriched sample may need to be prepared or processed prior to analysis, using known methods. For example, bacterial colonies may be removed, separated or isolated from the culture medium. If the culturing is carried out in a broth, separation of the bacterial colonies may involve centrifugation of the broth and, removal of the supernatant liquid, such as in the enrichment process discussed above.

Preferably the centrifugation step in the enrichment process comprises a centrifugation and pooling protocol, to improve the separation of the solid and liquid components of the sample-containing broth.

This protocol comprises:
dividing the sample-containing broth into a plurality of aliquots;
centrifuging the aliquots; discarding the resultant supernatants;
re-suspending the pellets in water;
pooling the resultant pellets; and
centrifuging a suspension of the pooled pellets, to separate the pellet containing the enriched sample.

Some examples of broths suitable for culturing bacteria are discussed above. Preferably the broth is prepared by reconstitution of a powdered microbiological culture material. More preferably, preparation of the broth involves reconstituting the broth in water, autoclaving the reconstituted solution at a temperature between 80 and 150° C., preferably from 110-125° C., most preferably about 120° C. or 121° C., for 10-30 minutes preferably about 15 minutes; leaving the solution to cool to a pre-determined temperature in the autoclave; removing the solution from the autoclave once this pre-determined temperature is reached and then allowing the solution to continue cooling at room temperature. The pre-determined temperature may vary depending on the nature of the broth, but is typically from 50-100° C., preferably from 60-90° C., more preferably around 80° C.

The incubation of the sample for culturing is preferably performed in a water bath i.e. by 'wet incubation'. The incubation is carried out at a pre-determined temperature for a pre-determined length of time. Advantageously this method allows culturing to be carried out for a short time period (less than 6 hours). More preferably, the sample is incubated for less than 4 hours, less than 2 hours or less than 1 hour. In some preferred embodiments, a culture time (incubation time) of from 30 minutes to 2 hours is used. The optimal temperature for incubation may vary depending on the organism to be cultured. In some preferred embodiments the temperature is from 25 to 60° C., more preferably from 30 to 40° C., or from 30 to 37° C. In some embodiments culturing is carried out at about 37° C. The temperature for incubation may be controlled by thermostatic control of the temperature of the water bath.

After enrichment as described above, analysis of the sample is preferably carried out using mass spectrometry, in accordance with the detection methods of the invention. In preferred embodiments, the analysis of the sample after short-term enrichment is performed using MALDI-TOF mass spectrometry, most preferably intact cell MALDI-TOF (ICM) analysis. In these embodiments preparation of the sample may involve applying bacterial isolates to a slide and layering with a suitable matrix material, as is known in the art.

The presence or absence of the particular bacteria of interest is determined in the methods of the invention by comparison of the profile data obtained from the mass spectrometric analysis of the short-term enriched sample with mass spectrometric reference data. The reference data is obtained from a reference sample of the bacteria of interest, which has been cultured and analysed, for example under analogous conditions to those which will be used on the test samples. In some embodiments the reference data comprises a reference mass-spectrometric profile obtained from a reference sample of a pre-determined bacterial infection/colonisation (i.e. the bacterial strain or species to be detected), which has been cultured for less than six hours. In some embodiments the reference data relates to pre-modification biomarkers, for example pre-modification proteins and/or peptidoglycans, produced by the particular bacteria. In some methods, the reference data relates to peaks in the mass spectrum of a short-term enriched reference sample of the bacterial species to be identified, in the region below about 1500 Da.

Reference data for a particular bacteria can be obtained from a reference sample of said particular bacteria. Any of the enrichment and analytical methods described herein for the test sample may equally be applied to a reference sample. For example, a reference sample may be obtained from a pure culture of the bacteria of interest, which may be sampled and subjected to short-term enrichment, as described herein.

Apparatus for performing the methods of the invention is also provided. Preferably the apparatus comprises a mass spectrometer and a data processor, the processor being programmed with said reference data for identifying one or more bacterial infections. The mass spectrometer is preferably a MALDI-TOF mass spectrometer.

In some preferred embodiments, the apparatus comprises an automated system for culturing a sample for subsequent analysis in the mass spectrometer. The automated system preferably comprises: an incubator for heating the sample during culturing; a temperature control device for controlling the temperature of the incubator; and a centrifuge for separation of the cultured sample from the culture medium.

DETAILED DESCRIPTION OF THE INVENTION

Figure 1:
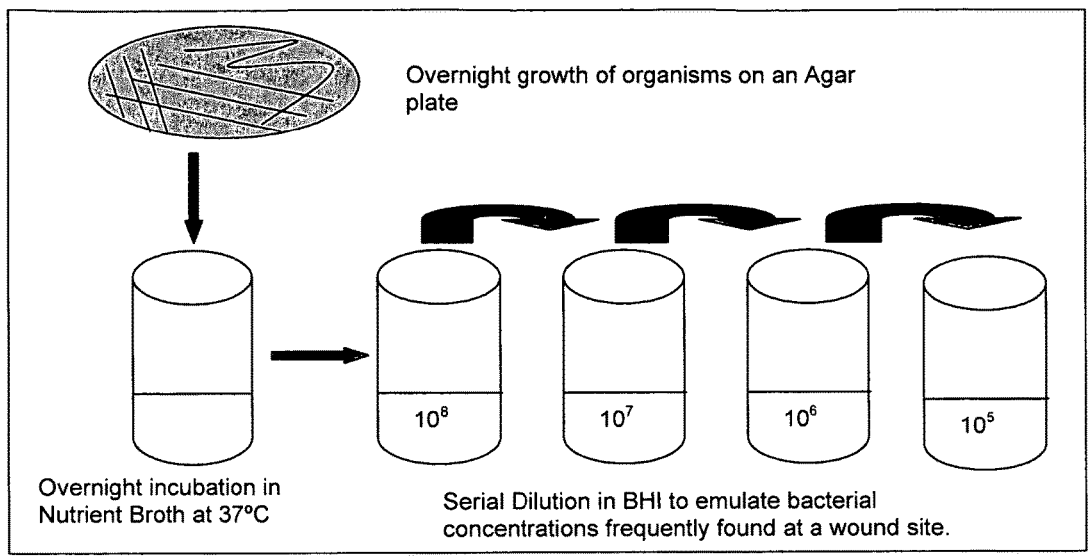
FIG. 1 illustrates the process of serial dilution of a culture in BHI broth, to emulate bacterial concentrations frequently found at a wound site.

The present inventor has found that biomarker profiles of bacterial species obtained after short-term enrichment culture are of use in the detection and diagnosis of infection or colonisation. These biomarker profiles can readily be examined by mass spectrometric analysis.

The biomarker profile data obtained and used in the methods of the invention may comprise proteomic profile data.

The term 'proteome' is commonly used to describe the entire complement of proteins produced by an organism or system, including modifications made to particular proteins. The proteome of an organism will vary with time, and will also depend on the various stresses that a cell or organism undergoes. As used herein, the term 'proteomic profile' refers to information about the protein content of a sample, as characterised by peaks in its mass spectrum corresponding to the proteins, glycoproteins, glycopeptides, peptidoglycans, and other species making up the proteome of the bacteria present in the sample. 'Proteomic profile data' is data relating to all or part of the proteomic profile of the sample, for example, mass spectrometric data, such as m/z values of peaks in the mass spectrum.

It is also possible that substances which are not proteins are represented in the mass spectrum, for example carbohydrates or lipo-polysaccharides, as well as glycoproteins, glycopeptides, peptidoglycans, and other species as mentioned above. For the sake of simplicity, however, the terms "proteomic profile" and "biomarker profile" may be used interchangeably herein, said profiles being represented by the peaks in the mass spectra of the bacteria.

In some preferred embodiments, the biomarker profile data comprises the values of peaks in the mass spectrum relating to the 'young' or 'early' biomarker profile of the sample i.e. to proteins and related molecules present in the sample after a short-term enrichment culture, as further explained herein.

Matrix-assisted laser desorption/ionization (MALDI) mass spectrometry is a well known technique which uses 'soft' ionization, so allowing the analysis of biomolecules (biopolymers such as proteins, peptides, peptidoglycans, sugars etc) which tend to fragment under conventional ionization conditions. Ionization is triggered by a laser beam (normally a nitrogen laser). A matrix is used to protect the biomolecule from being destroyed by the beam, and to facilitate vaporization and ionization. The matrix consists of crystallized molecules.

The identity of suitable matrix compounds is determined to some extent by trial and error and depends on the sample to be analysed, as is known in the art. However, conventional matrix materials are generally of a low enough molecular weight to allow facile vaporization but have a low enough vapour pressure not to evaporate during sample preparation or while standing in the spectrometer. They are also generally acidic molecules, thus acting as a proton source to encourage ionization of the analyte, and have strong UV absorption, so that they rapidly and efficiently absorb the laser irradiation. They may be functionalized with polar groups, allowing their use in aqueous solutions.

Commonly used matrices are 3,5-dimethoxy-4-hydroxycinnamic acid (sinapinic acid), α-cyano-4-hydroxycinnamic acid (alpha-cyano or alpha-matrix) and 2,5-dihydroxybenzoic acid (DHB), picolinic acid (PA) and 3-hydroxy picolinic acid (HPA). For applications with MRSA, a preferred matrix is 5-chloro-2-mercaptobenzothiazole (CMBT).

In a standard method of sample preparation, a solution of one of these matrix molecules is made, often in a mixture of highly purified water and an organic solvent (normally acetonitrile or ethanol). The matrix solution is then mixed with the analyte (i.e. the sample) and this solution is spotted onto a MALDI plate. The solvents vaporize, leaving the matrix and analyte co-crystallized in a MALDI 'spot', on which the laser is fired to produce the ions which are then detected and analysed. The mass-to-charge ratio of the particles can be calculated based on behaviour of the ions as they pass through the electric and magnetic fields generated by the MS instrument.

Typically, a time-of-flight (TOF) analyzer uses an electric field to accelerate ions through the same potential, and then measures the time they take to reach the detector. If the particles all have the same charge, the kinetic energies will be identical, and their velocities will depend only on their masses. Lighter ions will reach the detector first.

Proteomic profiles of bacterial organisms, obtained by MALDI-TOF-MS analysis, have previously been obtained and used for typing and discrimination of bacterial organisms, including Staphylococci (References 10-14). In general, bacterial proteomic profiles for analysis have been obtained only after a long-term (usually overnight) culturing process. For example, a technique for acquiring a mass spectrometric 'fingerprint' of MRSA was developed (Reference 11) in which the optimum fingerprint was achieved after 18-24 hours incubation, although a 6 hour incubation period was also tested.

The mass spectrometry-based techniques currently used in bacterial typing are not easily applicable to direct analysis of clinical samples. Typing work is primarily aimed at identifying bacteria in an epidemic setting, not at a clinical diagnosis. Therefore, the timescale for typing is not usually critical—up to 24 hours can be taken to perform a typing analysis, without this making a huge difference to the outcome for patients. Conversely, the time taken for detection and diagnosis in a clinical setting is more important since it can make a difference to the outcome for patients.

The proteomic profile produced in the typing work, after a 24 hour culture of MRSA, comprises characteristic 'biomarker' peaks, which are predominantly in the higher molecular weight region of the spectrum. The proteins responsible for these peaks have not been identified but it is thought that they could represent mature (i.e. after post-translational modification) bacterial cell wall proteins. The biomarker peaks used in the prior art cannot be reliably detected from cultures after only two hours.

GB 2 438 066 A (Bruker Daltonik GmbH) describes a method of measuring the resistance of microbes to specific antibiotics, which involves incubating said microbes in an antibiotic-containing medium and subsequent analysis by mass spectrometry. Incubation times of around two hours are suggested. In this time the effect of the antibiotic in the medium (if any) on the growth of the bacteria can be assessed. However, there is no suggestion that a stable and reproducible diagnostic biomarker profile can be obtained, starting from a clinical sample, in this timeframe. Rather, this method looks at changes in the mass spectrometric profile (typically in the 5,000-20,000 Da range) caused by the presence of the antibiotic. The mass spectra from these incubated samples is compared to spectral libraries, which typically comprise reference data from 'mature' colonies e.g. 24 hour cultures.

The present inventor has now surprisingly found that diagnostically useful biomarker profile data can be reproducibly obtained after short-term enrichment (i.e. after only a few hours culturing). This has opened up, for the first time, a real possibility for providing an automated, relatively foolproof, method for the rapid diagnosis of infections using mass spectrometry, which will be usable in a real-life clinical setting such as a public hospital.

Figure 8:
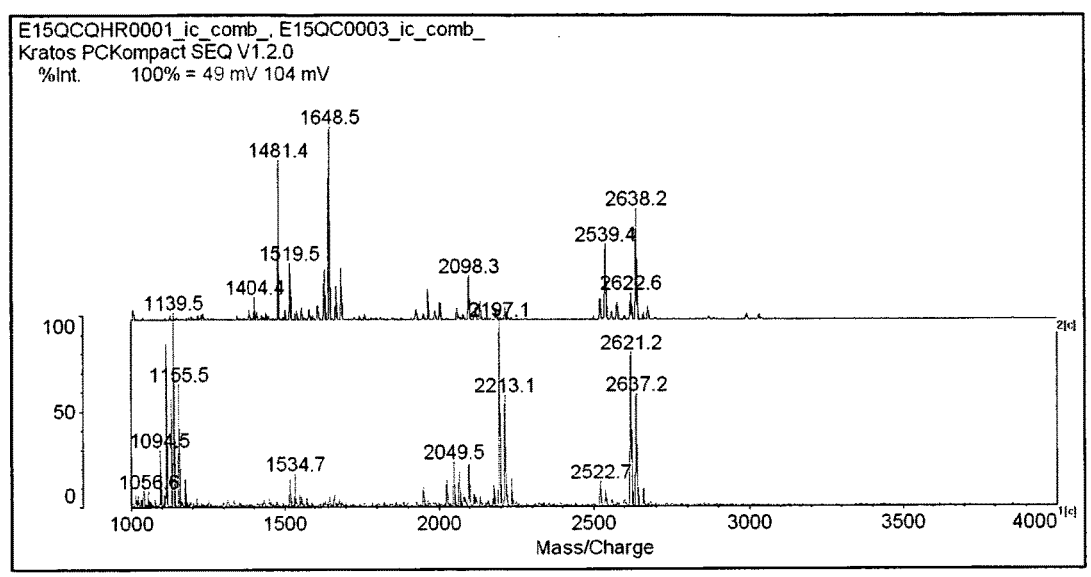
FIG. 8 compares overnight growth on an agar plate (top) to profiles obtained after enrichment at 4 hours (bottom) of the same bacterium Endemic Methicillin Resistant *Staphylococcus aureus* 15 (EMRSA15) in the mass range of 1-4 kDa.

The peak profiles obtained after short-term culture are significantly different to those obtained at 24 hours growth, containing a much larger number of low molecular weight (e.g. m/z below 1500; molecular mass below 1500 Da) peaks (e.g. FIG. 8). These low molecular weight peaks are not present in the proteomic profiles obtained after long-term (overnight) culture. It is thought that the lower molecular weight area of the mass spectrum has never previously been looked at or studied.

Without wishing to be bound by theory, it is thought that the low molecular weight peaks, found in the short term enriched biomarker profile, represent bacterial proteins or peptidoglycans, probably from the bacterial cell wall, in an unmodified state—i.e. before post-translational modification. These peaks represent unique biomarkers which are useful for fast detection and identification of bacteria in clinical samples. In some cases, further unique biomarker peaks, in the higher mass range of the spectrum, corresponding to pre-modification biomarkers of higher molecular weight, may also be present in the short-term enriched biomarker profile.

Post-translational modification (PTM) is the chemical modification of a protein after its translation and is one of the later steps in protein biosynthesis for many proteins. After translation, in which proteins are produced in the cell by decoding mRNA produced from transcription of the genome, post-translational modification then extends the range of functions of the protein by attaching to it other biochemical functional groups such as acetate, phosphate, various lipids and carbohydrates, by changing the chemical nature of an amino acid (e.g. citrullination) or by making structural changes, like the formation of disulfide bridges. In the case of bacterial cell wall proteins, an important post-translational modification is glycation of the peptides, i.e. the addition of a sugar molecule to the protein.

It is proposed that the proteins present in a 'young' bacterial sample, i.e. a sample which has been subjected to only short-term enrichment, may contain a higher proportion of unmodified peptides ('pre-modification') i.e. peptides which have been produced by translation but have not yet been modified to their final form.

Similarly, it is proposed that other biomarkers may be different in 'young' samples because a biomarker species has been produced by the bacteria but has not yet been modified to its final form, i.e. the form found in mature bacteria. A sample which has been subjected to only short-term enrichment may therefore contain a higher proportion of unmodified biomarkers ('pre-modification') i.e. biomarkers which have been produced but not yet been modified to their final form.

Given the transient nature of these unmodified species, it would not have been expected that a biomarker profile obtained after only a few hours would be reproducible and characteristic of the presence of a particular type of bacteria.

The present inventor has shown, however, that samples containing a low concentration of bacteria (e.g. $10^5$ cfu/ml—typical of clinical samples, such as from a wound site) can be cultured for a short time period, for example for 2 hours or less, and that the resultant 'short-term enriched' sample produces a useful diagnostic biomarker profile when the sample is subjected to proteomic analysis, for example an intact cell MALDI-TOF (ICM) analysis. Even shorter culture times and smaller numbers of organisms are also envisaged.

As used herein the term 'enrichment' refers to a process of increasing the number of bacteria present in the sample i.e. by culturing in a suitable medium. 'Short-term enrichment' implies that the culturing is carried out for a relatively short time period, as compared to conventional bacterial culturing, which generally takes place overnight. Typically, short-term enrichment means culturing the sample for less than 6 hours. Shorter culture times are more preferred, for example 4 hours or less, 2 hours or less, 1 hour or less, 30 minutes or less. A typical culture time is from 30 minutes to 2 hours. The 'culture time' is measured from the moment that the bacteria-containing (or suspected bacteria-containing) sample is inoculated into a culture medium. The sample may be heated (incubated) at a pre-determined culture temperature for all or part of the culture time. In the methods of the invention, culturing ends when the bacteria-containing portion of the enriched sample is separated from the culture medium.

Figure 6:
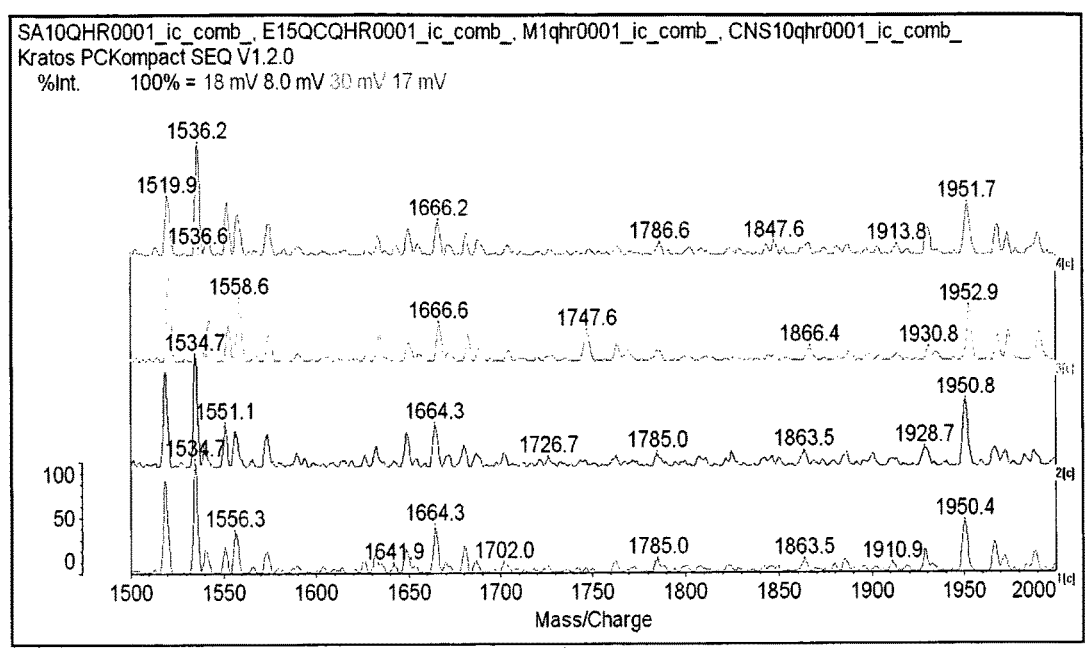
FIG. 6 shows the provisional diagnostic profiles for four bacteria (from top): *Staphylococcus aureus* (MSSA), Endemic Methicillin Resistant *Staphylococcus aureus* 15 (EMRSA15), Endemic Methicillin Resistant *Staphylococcus aureus* 16 (EMRSA15) and Coagulase negative Staphylococci (CNS), after short term enrichment at 4 hours in the mass range of 1.5-2 kDa.

As shown in more detail in the Examples, below, a 'young' (short-term enriched) biomarker profile for several *Staphylococcus* strains has already been established (FIG. 6) and has been shown to be maintained with 100% reproducibility, in the mass range of 1-4 kDa, across the spectrum of short-term enrichment (2 to 6 hours enrichment).

Results were obtained using optimised short-term enrichment culture conditions consisting of a custom culture broth, prepared from readily available starting materials, as set out in the Examples, below. There are a wide variety of broth based media available, in addition to the BHI (Brain Heart Infusion) broth used in this example. Other broths such as Mueller-Hinton Broth, Anaerobic broth and Nutrient Broth may also be used. Broths enriched with antibiotics may be useful, to ensure selective growth of the bacteria of interest (the bacterial infection to be detected), thus simplifying the analysis. The best conditions for performing the culture will depend on the organism to be detected.

Conventional broths are commercially available and can be obtained ready prepared in liquid form. Alternatively, the microbiological culture materials making up the broth can be obtained in powder form and re-constituted, as is known in the art. The present inventor has found that better results are achieved if the broth is carefully prepared, from powdered starting materials, using a new method. Conventionally, the powdered ingredients are reconstituted in distilled water and then sterilised by autoclaving. Autoclaving is carried out at high temperature, for example at around 120° C., although this may vary depending on the broth being prepared. The broth is then left to cool to room temperature before use. It is usual to leave the reconstituted solution in the autoclave until it has reached room temperature and is cool enough to be handled, which typically takes around two to three hours.

However, the present inventor has found that if the solution is removed from the autoclave at a higher temperature, a better broth, which gives better results for short-term culturing, is obtained. Without wishing to be bound by theory, it is thought that leaving the broth in the higher temperatures within the autoclave results in the meat in the broth being broken down into smaller molecules, which are difficult for the bacteria to consume, and that there may be some other inhibiting factor which is released which decreases growth in the first two to four hours of culturing.

The culture medium, for example as prepared above, is inoculated with the sample to be tested and the sample is cultured, to increase the amount of bacteria present in the sample. Conventional methods for the culturing of bacteria, particularly MRSA, tend to use a dry incubation i.e. incubation in a dry environment such as a dry incubator. Dry incubation relies on convection as a means of heating the medium and hence is non-uniform. Colder areas on the plate/broth may be present which will affect the growth of bacteria in those areas. The use of 'wet incubation', i.e. incubation in a water bath or similar environment, may be messier, but it is thought that it ensures uniform heating of the culture media, which helps the bacteria to grow more quickly. The temperature at which the water bath is set will vary depending on the culture conditions to be used. These can be optimised for each organism to be detected. Typically, temperatures close to human body temperature (i.e. 37° C.) are used, although MRSA can be cultured temperatures of 30-60° C.

The bacteria content in the cultured sample is analysed after culturing to obtain its biomarker profile. In conventional culture methods, using Agar based media, visualisation of the bacterial colonies growing on the plate or slope is needed, in order for these colonies to be picked out from the medium and analysed. In the preferred method of the present invention, a broth culture medium is used, and a new method of separating out the bacteria-containing material from the medium by centrifugation has been developed. For example, the cultured sample is split into several aliquots (for example, a 10 ml sample can be split into ten 1 ml aliquots (see FIG. 2) and centrifuged at 13,500 rpm for about three minutes in a microcentrifuge. The supernatant can be discarded and the pellets are then re-suspended in about 10 µl water. The resuspended aliquots are pooled together. The pooled sample is then re-centrifuged (e.g. at 13,500 rpm for a further three minutes) and the resulting pellet is used for mass spectrometric analysis. As will be clear to the person skilled in the art, a short-term enriched sample obtained in this way could equally be subjected to other types of analysis, as well as mass spectrometry. For example, applying the PCR-based methods, or latex agglutination methods, discussed earlier, to a culture prepared in only two hours, according to the present method, could potentially improve the speed and sensitivity of these methods of diagnosis.

In some embodiments, the culture medium is preferably free of antibiotics i.e. culturing is performed in a non-selective manner. The presence of antibiotics in the culture medium would have an effect on the nature of the protein biomarkers expressed, especially in the pre-translationally modified biomarker stage. Use of antibiotics is known to suppress the expression of certain biomarkers, and would generally be expected to slow the growth of the bacteria in the sample.

The optimal conditions for short-term enrichment may vary, depending on the organism. The method is applicable to both laboratory and clinical bacterial samples.

As will be clear to those skilled in the art, diagnostic biomarker profiles for other bacterial strains are obtainable in a similar manner as has been described for MRSA. The mass spectrometric profile data thus generated can be used as reference data in the detection methods of the invention. 'Reference data' therefore preferably comprises a mass spectrometric profile, or information about particular peaks in the mass spectrometric profile, which has been obtained for a short-term enriched reference sample, known to contain a particular bacteria of interest. A reference sample may comprise a sample from a pure culture of the bacteria of interest, which may have been diluted to a suitable concentration (i.e. comparable to the expected concentration of the bacteria at a screening site). The reference sample is added to a culture medium and subjected to short-term enrichment, as described above, to generate the reference biomarker profile.

The test described herein has the potential to detect the presence of particular bacteria at femtomole to picomole concentration of bacterial molecules. The cost of the test compares very favourably with previous methods, which can be very expensive and time-consuming. With the method of the present invention, the time to diagnosis (from wound concentration of bacteria to result) may be obtainable, for example, within two hours of the sample being taken.

A rapid diagnosis of a suspected bacterial infection or colonisation using MALDI-TOF and short term enrichment is therefore obtainable using the methods of the invention. In general, diagnosis may involve the following steps:

Step 1: A swab (or other sample) is taken from a patient. The type of swab/sample may be varied depending on the type of organism to be detected. However, it is envisaged that one uniform swab can be developed so that, irrespective of what organism is being tested for, the same swab will still be suitable.

Step 2: The sample is inoculated into enrichment medium. The culture medium and time period for enrichment can be chosen depending on the type of bacteria. If a broth culture is used, the sample may be collected after culturing by a centrifugation/pooling process.

Step 3: The enriched sample is subjected to MALDI-TOF analysis. A profile is obtained and analysed by comparison with reference data for the suspected bacterial infection. Different organisms will produce different profiles. Profiles may also differ slightly depending on the exact culture conditions used, although the general 'early stage' profile will remain the same for each organism. The reference data to which the obtained sample profile data is compared is chosen accordingly.

Step 4: The result of the analysis is obtained from the MALDI-TOF analysis—either positive (the suspected bacteria are present) or negative (the suspected bacterial infection is not present).

It is envisaged that the majority of steps of this process can be automated. For example, all of the steps after inoculation of the sample into the appropriate culture medium may be performed in a custom built MS analysis machine, pre-programmed with the appropriate conditions (i.e. culture temperatures(s), time, centrifugation protocol) for short-term enrichment of a number of bacteria, and with the reference data for identifying the biomarker profiles of those bacteria. Alternatively, an automated system for performing the short-term enrichment may be provided, for use in conjunction with an existing mass spectrometer.

The sample in the culture medium will be placed in the machine, and the appropriate program selected depending on the organism to be detected. The machine then heats the sample to the appropriate temperature for culturing, for example by immersing it in a water bath set at the appropriate temperature. After a pre-determined culture time (e.g. 30 minutes to 2 hours), the machine will automatically perform the necessary steps to prepare the sample for analysis. For example, the sample may be subjected to centrifugation, as described above, and the resulting solid sample transferred to a MALDI slide, within the machine. This may be done using a robotic system, for example.

This method shows the potential of mass spectrometry as a tool for rapid diagnosis of bacterial infections/colonisations, such as MRSA. Preservation of the bacterial diagnostic profile in isolates after short-term enrichment is a significant development and raises the possibility for the first time of wound swab to diagnosis within six hours, which has the potential to revolutionize the isolation of patients and the endemicity of MRSA in hospitals and the community.

EXAMPLES

Materials

The following ready prepared microbiological culture materials were obtained from Oxoid, Basingstoke, UK: Nutrient Broth B00210E and Columbia Agar with Horse Blood PB0122.

Brain Heart Infusion Broth CM0225 for the short term enrichment method was made as follows.

Reconstitution of the powder: The powder was commercially obtained from Oxoid. This was reconstituted by mixing 37 gm of the dry powder with one liter of distilled water.

Autoclaving: The reconstituted solution was autoclaved at 121° C. for fifteen minutes. The solution was removed from the autoclave when the temperature reached 80° C. (approximately fifteen to twenty minutes), then allowed to cool at room temperature for a further twenty to thirty minutes.

Bottling: The autoclaved reconstituted powder was then bottled using aseptic precautions into sterile glass containers.

This method of preparation showed consistently reproducible results.

Isolates used:
EMRSA 15 (Epidemic meticillin resistant *Staphylococcus aureus* phage-type 15)—ten isolates,
EMRSA 16 (Epidemic meticillin resistant *Staphylococcus aureus* phage-type 16)—ten isolates,
MSSA (Meticillin sensitive *Staphylococcus aureus*)—ten isolates,
Coagulase negative Staphylococci (CNS)—ten isolates
Other Endemic MRSA's-ten isolates Every isolate was tested in quintuplet and at concentrations of $10^5$ colony forming units (cfu) as described in the methods section below. Profiles obtained after twenty four hours growth on a Columbia Blood Agar (CBA) were used as a comparative control.

Preparation of Matrix Solution:

The matrix is used to ionize the proteins within the sample which is needed to help with separation of the molecules in the TOF tube. The optimal method of preparation of the matrix solution was published in 2005 (Reference 14). The matrix used was 5-chloro-2-mercaptobenzothiazole (CMBT) in a concentration of 3 mg/ml.

Example 1—Validation of the Method and Acquisition of Reference Data

Figure 2:
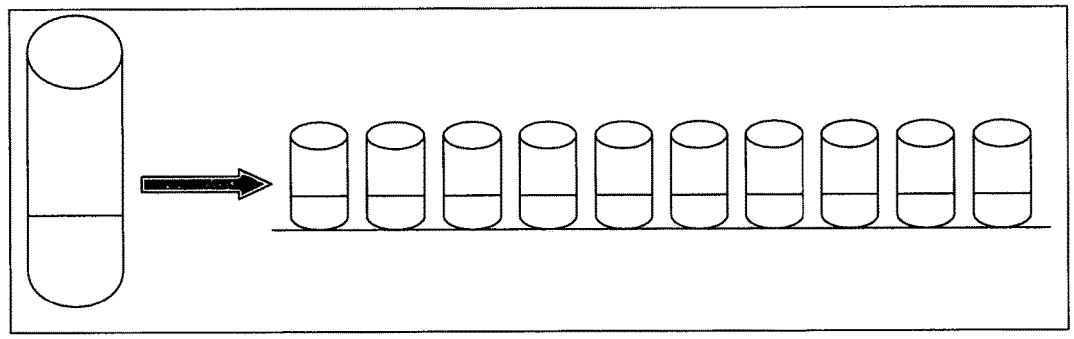
FIG. 2 illustrates the division of a short-term enriched sample into ten aliquots. Ten aliquots of one milliliter are created from one sample of ten milliliters.
Figure 3A:
FIG. 3 illustrates the preparation of a MALDI-TOF slide: (a) A Kratos Kompact twenty well MALDI-TOF slide is used. Each well is 2 mm in diameter. (b) The slide was layered with the bacterial isolates. (c) The bacterial layered slide was allowed to dry. (d) This slide was layered with matrix (CMBT) in two serial applications. (e) The matrix layered slide was allowed to dry, for up to 45 minutes, before it was introduced into the MALDI-TOF for analysis.
Figure 3B:
Figure 3C:
Figure 3D:
Figure 3E:

The following steps were tested:
1. Short term enrichment.
2. Collection and cleaning of sample
3. MALDI-TOF processing.
4. Analysis 1. Short Term Enrichment:

Short term enrichment was carried out as described below:

The organisms were sub-cultured and grown overnight at 37° C. Columbia Blood Agar (CBA) to obtain a pure culture for further work. A single colony was inoculated into Nutrient Broth and incubated at 37° C. overnight to obtain an approximate concentration of bacteria of $10^8$ colonyforming units/milliliter. To determine the limits of detection serial dilutions were carried out in Brain Heart Infusion (BHI) Broth, the broth used for the short term enrichment. This process is illustrated in FIG. 1. The serial dilutions result in samples with bacterial concentrations emulating those found at a wound site. These samples were then incubated for a period of two hours in a water bath at 37° C. The short-term enriched samples are then prepared for MALDI-TOF analysis as follows:

2. Collection and Cleaning of Sample:

Step 1: After short term enrichment for two hours, all the sample of each isolate was divided into ten one milliliter aliquots, as shown in FIG. 2.

Step 2: All the aliquots were then centrifuged at 13500 rpm for three minutes in a microcentrifuge.

Step 3: The supernatant was discarded and the pellet retained.

Step 4: 10 μl of water was added to the pellet and resuspended. All ten resuspended aliquots were pooled together. This was done for each isolate.

Step 5: The pooled sample was then re-centrifuged at 13500 rpm for three minutes.

Step 6: The resulting pellet from the pooled sample was then used for MALDI-TOF analysis.

3. MALDI-TOF Work:

All analysis was carried out after short term enrichment using the Kratos Kompact MALDI 2 linear, bench-top instrument. A twenty well Kratos Kompact MALDI-TOF slide was cleaned and prepared using the method optimized by Jackson et al (Reference 14). This is shown in FIG. 3.

The method of preparation of the slide was as follows:

Step 1: The slide was layered with the bacterial isolates after short term enrichment at two hours, until all the pellet was used.

Step 2: The bacterial layered slide was then allowed to dry.

Step 3: This slide was then overlaid with matrix (CMBT) in two serial applications of 0.5-1 μl each.

Step 4: The matrix layered slide was allowed to dry for 45 minutes before it was introduced into the MALDI-TOF for analysis All work was repeated at two, four, six and twenty four hours.

Figure 4:
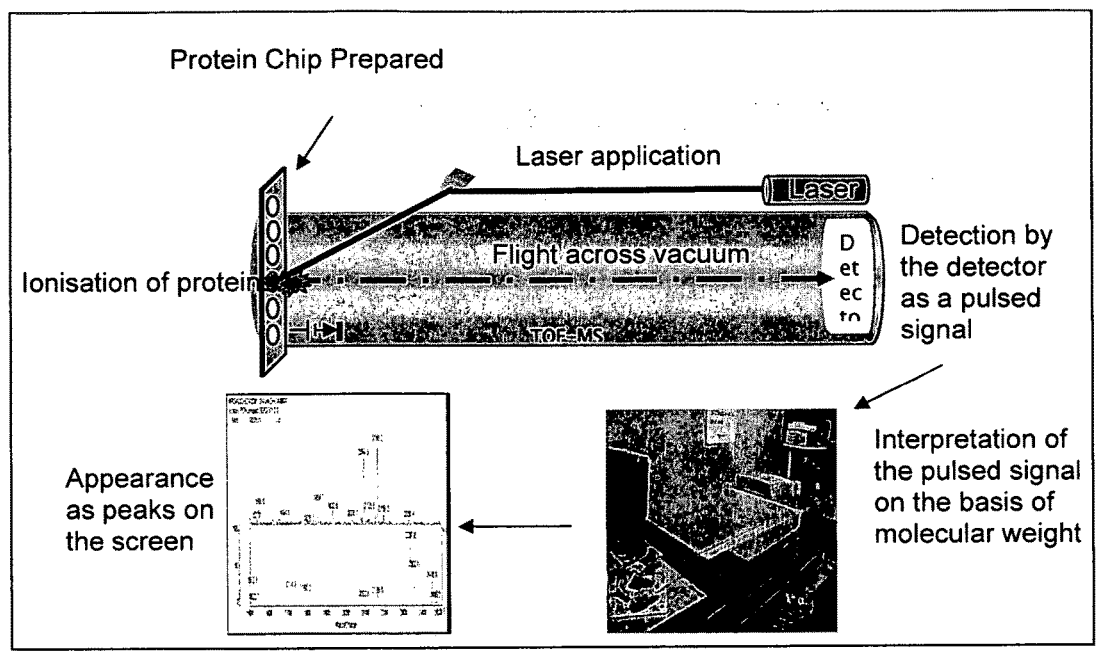
FIG. 4 demonstrates the working of a MALDI-TOF spectrometer.

Acquisition of data: The Kratos Kompact MALDI 2 is a linear, bench-top instrument (FIG. 4). The instrument is equipped with a nitrogen laser (337 nm, 3 ns pulse width). The laser energy was adjusted to above the threshold of ionization, enabling a balanced spectrum with peaks observed in the 800-4000 Da mass range of interest. Ions were accelerated in the positive ion mode with an accelerating voltage of +20 kV. The pulsed extraction of ions was optimized for 1000 Da. In all instances five replicate spectra were obtained. For each replicate 100 laser shots were accumulated by rastering across the width of the sample well.

Figure 5:
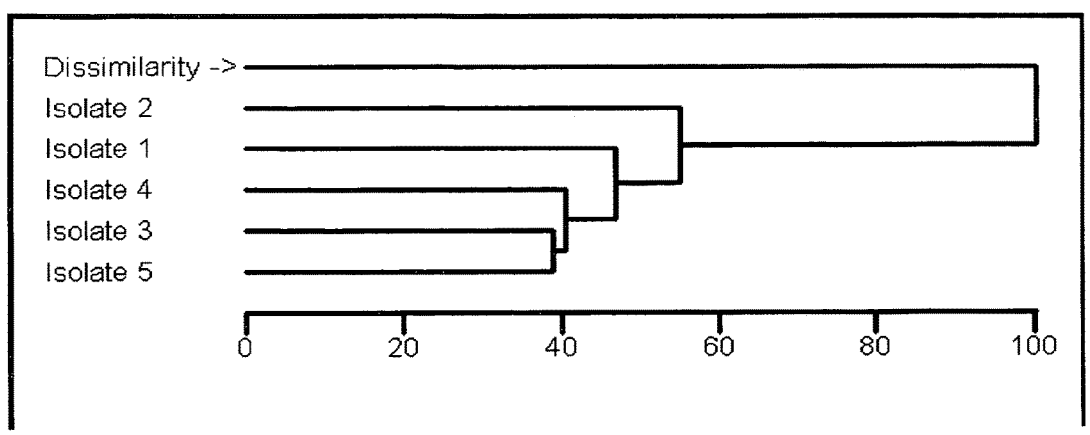
FIG. 5 shows the result of a cluster analysis for sequence dissimilarity on five replicates of one isolate.

4. Data Analysis:

MALDI-TOF based analysis: The Intact cell MALDI spectrum was obtained from 100 profiles acquired over the 2 μm spot on the target slide. These profiles were compiled automatically by the instrument to form an average profile for the replicate. Five replicates were obtained for each isolate, representing data compiled from 500 individual profiles. Once these replicates were obtained using the analysis tools within the MALDI-TOF instrument the following was carried out:

a) Determining the 'Best Replicates' Using Cluster Analysis:

Using prototype analytical tools, the 5 replicates were subjected to cluster analysis using a modified Jaquard algorithm designed to accommodate the large data set (over 16000 data points) and to take into consideration the operational issues associated with the instrumentation. Using this algorithm with the following parameters (cut off parameters; threshold of 0.5 mV, a mass range of 500 daltons to 10000 daltons and a threshold ratio of 4 (only those peaks with a baseline to peak ratio of greater than 4 were included)) the replicates were clustered and those with a sequence dissimilarity of greater than forty percent were discarded from the next step of analysis (FIG. 5).

b) Combining Files:

Only those replicates with sequence dissimilarity of less than forty percent were included in this element of the analysis. These replicates were then used to create a combined file using a preset programme within the Kratos Kompact MALDI-TOF software. The data from these combined files was used for all further analysis.

This pattern was maintained for each isolate of every species and for all the data obtained from two, four, six and twenty-four hour work. The broths which were used for the control experiments were also subjected to the same data analysis.

Manual Analysis Once the combined files were obtained for each of the isolates the following was carried out:

a) Formulation of Mass Lists:

Each combined file consisted of peak profiles that were unique to each isolate. Each profile contained within it a list of the peak masses. This is the mass list. The peak list of the combined file of an isolate is shown below.

shtermmar07dhr
CMBT E15FSCDHR
Data: E15FSCdhr0001_ic_comb_.16
13 Mar 2007 16:08 Factory calibrated
Kratos PCKompact SEQ V1.2.0: + Linear High,
Power: 80, P.Ext. @ 1046 (bin 57)

| Mass | % Total | Apex (mV) |
|---|---|---|
| 1017.59 | 0.39 | 1.56 |
| 1026.07 | 0.18 | 0.83 |
| 1034.28 | 0.12 | 0.81 |
| 1041.30 | 0.54 | 2.26 |
| 1046.19 | 0.11 | 0.79 |
| 1057.25 | 0.17 | 0.84 |
| 1095.17 | 1.32 | 6.06 |
| 1111.53 | 0.09 | 0.81 |
| 1116.28 | 4.92 | 22.69 |
| 1132.48 | 3.06 | 13.93 |
| 1140.14 | 4.07 | 16.16 |
| 1155.87 | 3.00 | 9.66 |
| 1162.00 | 0.18 | 1.21 |
| 1167.17 | 0.06 | 0.64 |
| 1170.08 | 0.12 | 0.78 |
| 1178.20 | 0.36 | 1.85 |
| 1194.19 | 0.05 | 0.63 |
| 1216.55 | 0.11 | 0.84 |
| 1229.14 | 0.08 | 0.66 |
| 1252.50 | 0.09 | 0.59 |

All peaks in the mass range of eight hundred daltons to five thousand daltons were noted for each of the ten isolates for each species of Staphylococci. This data was then transferred to a spreadsheet as shown in Table 1 below, which is an example of a mass list created from the combined files for the ten isolates of S. aureus.

TABLE 1

| SA1 | SA2 | SA3 | SA4 | SA5 | SA6 | SA7 | SA8 | SA9 | SA10 |
|---|---|---|---|---|---|---|---|---|---|
| 1017.29 | 1008.24 | 1017.86 | 1001.93 | 1001.93 | 1008.84 | 1017.59 | 1001.93 | 1018.47 | 1010.05 |
| 1023.94 | 1017.29 | 1024.86 | 1009.14 | 1004.33 | 1018.49 | 1024.85 | 1010.05 | 1025.47 | 1016.98 |
| 1026.07 | 1024.25 | 1034.33 | 1019.4 | 1010.05 | 1025.16 | 1033.97 | 1018.19 | 1034.33 | 1020.31 |
| 1033.67 | 1033.67 | 1041.39 | 1024.85 | 1017.59 | 1034.28 | 1040.99 | 1025.46 | 1041.7 | 1024.55 |
| 1040.07 | 1040.99 | 1095.55 | 1033.97 | 1024.25 | 1040.99 | 1057.56 | 1034.28 | 1057.74 | 1033.67 |

TABLE 1-continued

| SA1 | SA2 | SA3 | SA4 | SA5 | SA6 | SA7 | SA8 | SA9 | SA10 |
|---|---|---|---|---|---|---|---|---|---|
| 1043.44 | 1056.95 | 1117.08 | 1040.99 | 1033.97 | 1057.56 | 1062.81 | 1040.99 | 1095.86 | 1040.38 |
| 1050.18 | 1063.11 | 1133.37 | 1057.87 | 1040.69 | 1078.93 | 1071.16 | 1057.56 | 1112.31 | 1047.11 |
| 1056.64 | 1067.75 | 1140.76 | 1062.5 | 1045.89 | 1095.17 | 1078.93 | 1062.5 | 1117.4 | 1051.1 |
| 1078.3 | 1071.47 | 1156.57 | 1064.35 | 1050.18 | 1111.53 | 1090.16 | 1078.93 | 1133.37 | 1057.56 |
| 1094.23 | 1078.93 | 1163.06 | 1068.37 | 1056.95 | 1116.59 | 1095.48 | 1095.48 | 1141.08 | 1061.88 |
| 1104.59 | 1083.29 | 1171.19 | 1073.33 | 1062.5 | 1132.48 | 1100.19 | 1099.25 | 1157.22 | 1068.99 |
| 1110.59 | 1087.66 | 1179.35 | 1078.62 | 1068.06 | 1140.14 | 1111.22 | 1105.22 | 1163.38 | 1071.47 |
| 1115.64 | 1094.86 | 1217.26 | 1084.22 | 1070.85 | 1156.19 | 1116.59 | 1111.53 | 1171.52 | 1078.62 | b) Use of Macros:

Once the mass lists were created for each of the five species of Staphylococci a specially designed macro within the spreadsheet was used to look for common biomarker peaks. This macro identified within a correct range peaks with 0.2% accuracy.

The common peaks could be highlighted as shown in Table 2 below. This aided visual identification.

TABLE 2

| SA1 | SA2 | SA3 | SA4 | SA5 | SA6 | SA7 | SA8 | SA9 | SA10 |
|---|---|---|---|---|---|---|---|---|---|
|  |  |  | 1001.93 | 1001.93 |  |  | 1001.93 |  |  |
|  |  |  |  | 1004.33 |  |  |  |  |  |
|  | 1008.24 |  | 1009.14 | 1010.05 | 1008.84 |  | 1010.05 |  | 1010.05 |
| 1017.29 | 1017.29 | 1017.86 |  | 1017.59 | 1018.49 | 1017.59 | 1018.19 | 1018.47 | 1016.98 |
|  |  |  | 1019.4 |  |  |  |  |  | 1020.31 |
| 1023.94 | 1024.25 | 1024.86 | 1024.85 | 1024.25 | 1025.16 | 1024.85 | 1025.46 | 1025.47 | 1024.55 |
| 1026.07 |  |  |  |  |  |  |  |  |  |
| 1033.67 | 1033.67 | 1034.33 | 1033.97 | 1033.97 | 1034.28 | 1033.97 | 1034.28 | 1034.33 | 1033.67 |
| 1040.07 | 1040.99 | 1041.39 | 1040.99 | 1040.69 | 1040.99 | 1040.99 | 1040.99 | 1041.7 | 1040.38 |
| 1043.44 |  |  |  |  |  |  |  |  |  |

For further reproducibility each of the lists were visually verified and any peaks that were not highlighted but were within five daltons of the lowest peak in the same mass range were added to the list of common peaks. Thus for each of the five species a list of peaks was drawn up which was common to all ten isolates of the same species.

c) Derivation of Final Diagnostic Profiles:

The final diagnostic profile which identified the peaks common to all the Staphylococci as well as those unique to MRSAs was drawn up by subjecting the common lists of each of the species to scrutiny by the same Excel macros spreadsheet.

This detailed analysis has been carried for all the bacteria at two, four, six and twenty four hours and diagnostic profiles have been obtained at each of these time points.

Figure 7:
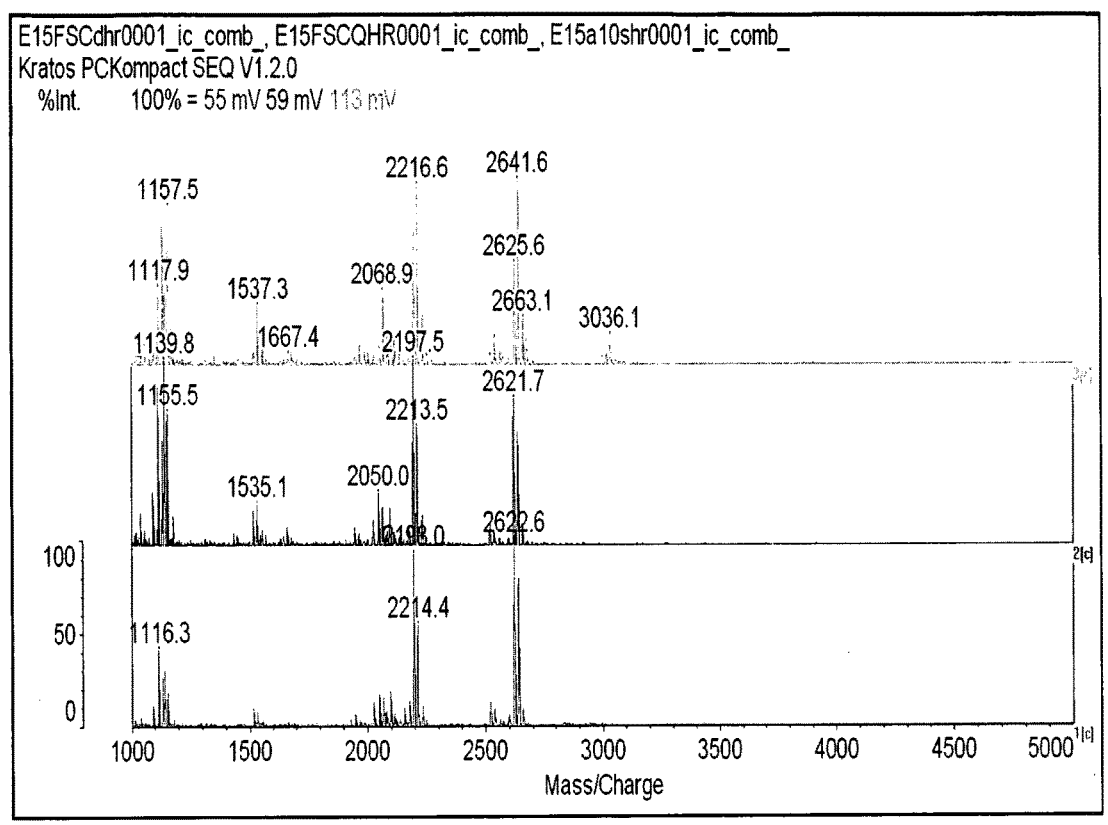
FIG. 7 demonstrates that the peak profile is maintained across the spectrum of short term enrichment. The profiles at the bottom of the figure are obtained at two hours, those in the middle at four hours and those at the top at six hours of the same isolate of *S. aureus*.

Results:

1) For the first time a provisional diagnostic profile for MRSA is proposed on the basis of proteomic analysis of laboratory based isolates after short term enrichment (FIG. 6).
2) The provisional diagnostic profile of MRSA is maintained in the bacteria in the mass range of 1-4 kDa with 100% reproducibility across the spectrum of short term enrichment (FIG. 7).)
3) A provisional diagnostic profile for MRSA at two hours:

Peaks that are common in all the isolates of Staphylococci:

1018.19, 1034.28, 1041.6, 1057.56, 1095.8, 1116.91, 1133.11, 1140.46, 1156.19, 1170.73, 1216.55, 1315.64, 1353.01, 1379.63, 1437.58, 1453.79, 1520.28, 1536.2, 1552.21, 1558.19, 1574.31, 1633.88, 1665.82, 1682.1, 1952.5, 1968.44, 1990.35, 2029.85, 2051.25, 2100.46, 2116.12, 2181.99, 2215.31, 2237.21, 2524.61, 2540.82, 2578.69, 2600.86, 2623.62, 2639.66, 2661.6, 2677.76

Peaks that, are unique to the isolates of MRSA:

1080.17, 1179.5, 1651.16, 1866.8, 1882.39, 1931.2, 2068.02, 2074.49, 2085.72, 2139.28, 2155.08, 2160.8, 2200.17, 2254.27, 2400.97, 2580.13, 2875.41

4) The peak profiles at short term are significantly different to those obtained at twenty four hours in agar plate growth (see FIG. 8).
5) The test has the potential to detect at femtomole to picomole concentration of molecular molecules from bacteria
6) Cost of the test is approximately 5 p/sample.
7) Time to diagnosis from wound concentration of bacteria to result can be obtained as early as two hours.

This test shows the potential of mass spectrometry as a tool for rapid diagnosis of MRSA.

Example 2—Validation of Results With Clinical Samples

1. Clinical swabs are taken—screening sites include nose, groin, axilla and perineum, as well as swabs from ulcers, blood cultures and tissues.
2. A portion of each sample is inoculated into custom BHI broth, prepared as in Example 1. For comparison, each sample is also cultured according to the 'gold standard' for MRSA detection i.e. culturing for 16-72 hours on selective or non-selective Agar plates.
3. The BHI broth samples is introduced into the automated prototype. Culturing is carried out for approximately 2 hours, by incubation in a water bath. Samples are prepared for analysis, as described in Example 1.
4. MALDI-TOF analysis is carried out to determine the MS profile of the samples. These are compared (e.g. by a data processor within the prototype) with the reference data (e.g. as shown in Example 1), to determine the presence or absence of MRSA.

5. Results are compared with the long-term culture 'gold standard' methods, using the following criteria: specificity, sensitivity, accuracy, false-positive rate, false-negative rate and cost economics.

REFERENCES

1) Ashimoto, A., T. Hamada, et al. (1995). "Molecular epidemiology of *Staphylococcus* spp. contamination in the ward environment: study on mecA and femA genes in methicillin-resistant strains." Kansenshogaku Zasshi 69(1): 15-20.
2) Brakstad, 0. G. and J. A. Maeland (1995). "Direct identification of *Staphylococcus aureus* in blood cultures by detection of the gene encoding the thermostable nuclease or the gene product." Apmis 103(3): 209-18.
3) Francois, P., D. Pittet, et al. (2003). "Rapid detection of methicillin-resistant *Staphylococcus aureus* directly from sterile or nonsterile clinical samples by a new molecular assay." J Clin Microbiol 41(1): 254-60.
4) Zhang, K., J. Sperling, et al. (2004). "New quadriplex PCR assay for detection of methicillin and mupirocin resistance and simultaneous discrimination of *Staphylococcus aureus* from coagulase-negative staphylococci." J Clin Microbiol 42(11): 4947-55.
5) Hardy, K. J., A. Szczepura, et al. (2007). "A study of the efficacy and cost-effectiveness of MRSA screening and monitoring on surgical wards using a new, rapid molecular test (EMMS)." BMC Health Sery Res 7: 160.
6) Jeyaratnam, D., C. J. Whitty, et al. (2008). "Impact of rapid screening tests on acquisition of meticillin resistant *Staphylococcus aureus*: cluster randomised crossover trial." Bmj 336(7650): 927-30.
7) Cunningham, R., P. Jenks, et al. (2007). "Effect on MRSA transmission of rapid PCR testing of patients admitted to critical care." J Hosp Infect 65(1): 24-8.
8) de San, N., O. Denis, et al. (2007). "Controlled evaluation of the IDI-MRSA assay for detection of colonization by methicillin-resistant *Staphylococcus aureus* in diverse mucocutaneous specimens." J Clin Microbiol 45(4): 1098-101.
9) Chediac-Tannoury, R. and G. F. Araj (2003). "Rapid MRSA detection by a latex kit." Clin Lab Sci 16(4): 198-202.
10) Edwards-Jones V, Claydon, M. A., Evason, D. J., Walker, J., Fox, A. J., and Gordon, D. B. (2000). "Rapid discrimination between methicillin-sensitive and methicillin-resistant *Staphylococcus aureus* by intact cell mass spectrometry" J. Med. Microbiol. 49, 295-300.
11) Jackson, K. A., Fox, A. J., Edwards-Jones, V. (2003) "Determination and structural examination of potential biomarkers for Methicillin-resistant *Staphylococcus aureus*." Applications of genomics and proteomics for analysis of bacterial biological warfare agents—IOS Press—Editors: DelVecchio, V. G., Krcmery, V
12) Smole S C, King L A, Leopold P E, Arbeit R D. "Sample preparation of Gram-positive bacteria for identification by matrix assisted laser desorplion/ionization time-of-flight." J Microbiol Methods 2002; 48: 107-15.
13) Bright J J, Claydon M A, Soufian M, Gordon D B. "Rapid typing of bacteria using matrix-assisted laser desorption ionixation time-of-flight mass spectrometry and pattern recognition software." J Microbiol Methods 2002; 48: 127-38.
14) Jackson, K. A., V. Edwards-Jones, et al. "Optimisation of intact cell MALDI method for fingerprinting of methicillin-resistant *Staphylococcus aureus*." J Microbiol Methods 2005, 62(3): 273-84.
15) UK Patent Publication GB 2 3438 066 A-Bruker Daltonik GmbH (14 Nov. 2007).
16) Bendy R H, Nuccio P A, Wolfe E, Collins B, Tamburro C, Glass W, Martin C M. "Relationship of quantitative wound bacterial counts to healing of decubiti. Effect of topical gentamicin." Antimicrob Agents Chemother. 1964; 4:147-155.
17) Hanft, Jason R. and Smith, Brigette, "How To Differentiate Between Infected Wounds And Colonized Wounds", Podiatry Today, 2005, 18, 7, 85-90.

The invention claimed is:

1. A method for detection of the presence or absence of particular bacteria in a clinical sample, the method comprising:
(i) enriching the clinical sample by culturing the bacteria present in the clinical sample for a period of time less than 6 hours such that pre-modification biomarkers are produced in the sample, wherein enrichment is carried out by:
inoculating the clinical sample into a broth;
culturing the clinical sample-containing broth for a period of less than 6 hours; and
separating an enriched clinical sample from the sample-containing broth by centrifugation, and
wherein said broth is prepared by a method comprising:
reconstituting a powdered microbiological culture material in water;
autoclaving the reconstituted solution at a temperature between 80 and 150° C.;
leaving the solution to cool in the autoclave to a pre-determined temperature of between 60 and 90° C.;
removing the solution from the autoclave when the predetermined temperature is reached; and
allowing the solution to continue cooling at room temperature;
(ii) analysing the enriched clinical sample by mass spectrometry, to obtain clinical biomarker profile data, wherein the clinical biomarker profile data comprises peaks of specific masses in the region below 1500 Da, corresponding to pre-modification biomarkers produced by bacteria in the clinical sample;
(iii) correlating the clinical sample biomarker profile data with reference data to look for peaks having specific masses in the region below 1500 Da common to the clinical sample biomarker profile data and to the reference data, to determine the presence of absence of said particular bacteria in the sample;
wherein a match between the masses of the peaks of the clinical sample biomarker profile data the reference data indicates the presence of a particular bacteria in the clinical sample,
wherein the reference data relates to pre-modification biomarkers represented by peaks having specific masses produced by a reference sample of said particular bacteria which has been cultured for less than six hours,
and wherein the concentration of bacteria in the clinical sample before enrichment is about $10^7$ cfu/ml or below.

2. The method according to claim 1, wherein the culturing in step (i) is carried out for four hours or less.

3. The method according to claim 1, wherein the culturing in step (i) is carried out for two hours or less.

4. The method according to claim 1, wherein the clinical sample is taken from a human patient.

5. The method according to claim 1, wherein said clinical sample biomarker profile data is proteomic profile data.

6. The method according to claim 1, wherein the analysis by mass spectrometry is performed using MALDI-TOF mass spectrometry.

7. The method according to claim 1, wherein culturing the clinical sample comprises incubation in a water bath.

8. The method according to claim 1, wherein the centrifugation step comprises:
dividing the clinical sample-containing broth into a plurality of aliquots;
centrifuging the aliquots;
discarding the resultant supernatants;
re-suspending the pellets in water;
pooling the resultant pellets; and
centrifuging a suspension of the pooled pellets, to separate the pellet containing the enriched clinical sample.

9. The method according to claim 1, wherein the broth is a Brain Heart Infusion (BHI) broth, a Mueller-Hinton Broth, an Anaerobic broth or a Nutrient Broth.

10. The method according to claim 1, wherein the analysis by mass spectrometry is performed using MALDI-TOF mass spectrometry, and further wherein the culturing in step (i) is carried out for four hours or less.

11. The method according to claim 10, wherein the culturing in step (i) is carried out for two hours or less.

12. The method according to claim 10, wherein the enriched clinical sample is obtained by
inoculating a bacteria-containing clinical sample into a broth,
culturing the clinical sample-containing broth for a period of 4 hours or less to produce an enriched clinical sample, and
separating the enriched clinical sample from the sample-containing broth by centrifugation.

13. The method according to claim 12, wherein culturing the clinical sample comprises incubation in a water bath.

14. The method according to claim 12, wherein the centrifugation step comprises
dividing the clinical sample-containing broth into a plurality of aliquots,
centrifuging the aliquots,
discarding the resultant supernatants,
re-suspending the pellets in water,
pooling the resultant pellets, and
centrifuging a suspension of the pooled pellets to produce the enriched clinical sample.

15. The method of claim 1, wherein the particular bacteria being detected is selected from the group consisting of Staphylococci, *Clostridium, Escherichia coli, Campylobacter, Salmonella, Pseudomonas, Shigella, Neisseria, Klebsiella, Vibrio, Legionella, Haemophilus influenzae, Helicobacter pylori, Bacillus, Listeria*, and bacteria causing tuberculosis and leprosy.

16. The method of claim 15, wherein the particular bacteria being detected is a Gram-positive bacteria.

17. The method of claim 16, wherein the particular bacteria being detected is a methicillin-resistant *Staphylococcus aureus* (MRSA).

* * * * *